(12) United States Patent
Carroll et al.

(10) Patent No.: US 6,482,182 B1
(45) Date of Patent: Nov. 19, 2002

(54) ANCHORING SYSTEM FOR A BRAIN LEAD

(75) Inventors: Catalina J. Carroll, Memphis, TN (US); Jaimie Henderson, St. Louis, MO (US); John B. Clayton, Superior, CO (US); Phillip T. Ulberg, Reno, NV (US)

(73) Assignee: Surgical Navigation Technologies, Inc., Louisville, CO (US)

( * ) Notice: Subject to any disclaimer, the term of this patent is extended or adjusted under 35 U.S.C. 154(b) by 0 days.

(21) Appl. No.: 09/389,130

(22) Filed: Sep. 2, 1999

Related U.S. Application Data

(60) Provisional application No. 60/099,119, filed on Sep. 3, 1998.

(51) Int. Cl.$^7$ ................................................ A61M 5/32
(52) U.S. Cl. ............. 604/174; 604/164.04; 604/165.02; 604/167.06; 607/116; 607/139; 607/149; 606/41; 606/129
(58) Field of Search ............................ 604/174, 164.04, 604/165.01, 165.02, 167.06, 264, 114; 600/114; 606/32, 41, 129, 130; 607/45, 116–118, 130, 139, 149

(56) References Cited

U.S. PATENT DOCUMENTS

| | | | |
|---|---|---|---|
| 4,328,813 A | 5/1982 | Ray | 128/791 |
| 4,506,676 A | 3/1985 | Duska | 128/653 |
| 4,583,538 A | 4/1986 | Onik et al. | 128/303 B |
| 4,602,622 A | 7/1986 | Bär et al. | 128/303 B |
| 4,608,977 A | 9/1986 | Brown | 128/303 B |
| 4,638,798 A | 1/1987 | Shelden et al. | 128/303 B |
| 4,673,352 A | 6/1987 | Hansen | 433/69 |
| 4,686,997 A | 8/1987 | Oloff et al. | 128/653 |
| 4,723,544 A | 2/1988 | Moore et al. | 128/303 B |
| 4,727,565 A | 2/1988 | Ericson | 378/205 |
| 4,733,661 A | 3/1988 | Palestrant | 128/303 B |

(List continued on next page.)

FOREIGN PATENT DOCUMENTS

| | | |
|---|---|---|
| DE | 197 15 202 A1 | 4/1997 |
| DE | 197 47 427 A1 | 10/1997 |

(List continued on next page.)

OTHER PUBLICATIONS

Olivier, et al., Frameless stereotaxy for surgery of the epilepsies: preliminary experience, Journal of Neurosurgery, Oct. 1994, 629–633, vol. 81, No. 4.

Smith, et al., The Neurostation™—A Highly Accurate, Minimally Invasive Solution to Frameless Stereotactic Neurosurgery, Computerized Medical Imaging and Graphics, Jul.–Aug. 1994, 247, 276–277, vol. 18, No. 4.

(List continued on next page.)

Primary Examiner—Brian L. Casler
Assistant Examiner—Jeremy Thissell
(74) Attorney, Agent, or Firm—Harness, Dickey & Pierce, P.L.C.

(57) ABSTRACT

A brain lead anchoring system is described which allows for installation of a brain stimulation lead or a drug delivery catheter without the lead or catheter ever being unsupported during installation so that the lead or catheter does not move during the anchoring procedure. An anchor assembly contains an anchoring mechanism that is biased in the closed or anchoring position and is only open to allow installation of a lead when it is mated to an introducer instrument, which has prongs that open the anchoring mechanism. Once the lead is appropriately positioned within the brain and while the lead is still supported by the installation guiding device, the introducer instrument is withdrawn from the anchoring mechanism, which thus allows the anchoring mechanism to return to its closed position. A locking cap covers the aperture through the anchor assembly into the skull and mechanically ensures that the anchoring mechanism remains in the closed position. The anchor assembly also has channels in its top surface within which the lead may be inserted so that the lead may be lain flat on the surface of the patient's skull.

22 Claims, 6 Drawing Sheets

U.S. PATENT DOCUMENTS

| | | | |
|---|---|---|---|
| 4,805,615 A | | 2/1989 | Carol .................... 128/303 B |
| 4,809,694 A | * | 3/1989 | Ferrara .................... 606/130 |
| 4,841,967 A | | 6/1989 | Chang et al. ............ 128/303 B |
| 4,875,478 A | | 10/1989 | Chen .................... 128/303 B |
| 4,931,056 A | | 6/1990 | Ghajar et al. ............... 606/130 |
| 4,952,214 A | | 8/1990 | Comparetto ................. 606/87 |
| 4,955,891 A | | 9/1990 | Carol .................... 606/130 |
| 5,047,036 A | | 9/1991 | Koutrouvelis ............... 606/130 |
| 5,078,140 A | | 1/1992 | Kwoh .................... 128/653.1 |
| 5,078,142 A | | 1/1992 | Siczek et al. ............ 128/653.1 |
| 5,116,345 A | | 5/1992 | Jewell et al. ............... 606/130 |
| 5,186,174 A | | 2/1993 | Schlöndorff et al. ..... 128/653.1 |
| 5,198,877 A | | 3/1993 | Schultz .................... 356/375 |
| 5,230,623 A | | 7/1993 | Guthrie et al. ................ 433/72 |
| 5,257,998 A | | 11/1993 | Ota et al. .................... 606/130 |
| 5,261,404 A | | 11/1993 | Mick et al. ............ 128/653.1 |
| 5,279,309 A | | 1/1994 | Taylor et al. ............... 128/782 |
| 5,305,203 A | | 4/1994 | Raab .................... 364/413.13 |
| 5,309,913 A | | 5/1994 | Kormos et al. ........... 128/653.1 |
| 5,370,623 A | * | 12/1994 | Kreamer ................. 604/165.02 |
| 5,383,454 A | | 1/1995 | Bucholz .................. 128/653.1 |
| 5,389,101 A | | 2/1995 | Heilbrun et al. ............ 606/130 |
| 5,399,146 A | | 3/1995 | Nowacki et al. ............... 601/4 |
| 5,402,801 A | | 4/1995 | Taylor .................... 128/898 |
| 5,447,154 A | | 9/1995 | Cinquin et al. .......... 128/653.1 |
| 5,464,446 A | | 11/1995 | Dressen et al. ............. 607/116 |
| 5,483,961 A | | 1/1996 | Kelly et al. ............... 128/653.1 |
| 5,494,034 A | | 2/1996 | Schlöndorff et al. ..... 128/653.1 |
| 5,515,160 A | | 5/1996 | Schulz et al. ................ 356/241 |
| 5,517,990 A | | 5/1996 | Kalfas et al. ............ 128/653.1 |
| 5,531,227 A | | 7/1996 | Schneider ................ 128/653.1 |
| 5,531,520 A | | 7/1996 | Grimson et al. ............ 382/131 |
| 5,551,429 A | | 9/1996 | Fitzpatrick et al. ...... 128/653.1 |
| 5,568,809 A | | 10/1996 | Ben-haim .................... 128/656 |
| 5,572,999 A | | 11/1996 | Funda et al. ............. 128/653.1 |
| 5,588,430 A | | 12/1996 | Bova et al. ............. 128/653.1 |
| 5,603,318 A | | 2/1997 | Heilbrun et al. ............ 128/630 |
| 5,617,857 A | | 4/1997 | Chader et al. ........... 128/653.1 |
| 5,622,170 A | | 4/1997 | Schulz .................... 128/653.1 |
| 5,630,431 A | | 5/1997 | Taylor .................... 128/897 |
| 5,638,819 A | | 6/1997 | Manwaring et al. ..... 128/653.1 |
| 5,647,361 A | | 7/1997 | Damadian ................ 128/683.2 |
| 5,662,111 A | * | 9/1997 | Cosman .................... 600/417 |
| 5,676,673 A | | 10/1997 | Ferre et al. ................. 606/130 |
| 5,682,886 A | | 11/1997 | Delp et al. ............... 128/653.1 |
| 5,695,500 A | | 12/1997 | Taylor et al. ............... 606/130 |
| 5,695,501 A | | 12/1997 | Carol et al. .................. 606/130 |
| 5,711,299 A | | 1/1998 | Manwaring et al. ..... 128/653.1 |
| 5,713,847 A | | 2/1998 | Howard, III et al. ......... 604/21 |
| 5,748,767 A | | 5/1998 | Raab .................... 382/128 |
| 5,749,362 A | | 5/1998 | Funda et al. ............. 128/653.1 |
| 5,755,725 A | | 5/1998 | Druais .................... 606/130 |
| 5,772,594 A | | 6/1998 | Barrick .................... 600/407 |
| 5,795,294 A | | 8/1998 | Luber et al. ................. 600/407 |
| 5,799,055 A | | 8/1998 | Peshkin et al. ................ 378/42 |
| 5,800,535 A | | 9/1998 | Howard, III ................. 623/10 |
| 5,823,958 A | | 10/1998 | Truppe .................... 600/426 |
| 5,833,608 A | | 11/1998 | Acker .................... 600/409 |
| 5,834,759 A | | 11/1998 | Glossop .................. 250/203.1 |
| 5,836,954 A | | 11/1998 | Heilbrun et al. ............ 606/130 |
| 5,843,150 A | * | 12/1998 | Dreessen et al. ............ 128/898 |
| 5,848,967 A | | 12/1998 | Cosman .................... 600/426 |
| 5,851,183 A | | 12/1998 | Bucholz .................... 600/425 |
| 5,865,842 A | * | 2/1999 | Knuth et al. ................ 601/116 |
| 5,868,675 A | | 2/1999 | Henrion et al. ............. 600/424 |
| 5,871,445 A | | 2/1999 | Bucholz .................... 600/407 |
| 5,871,487 A | | 2/1999 | Warner et al. ............... 606/130 |
| 5,891,157 A | | 4/1999 | Day et al. .................... 606/130 |
| 5,904,691 A | | 5/1999 | Barnett et al. ............... 606/130 |
| 5,920,395 A | | 7/1999 | Schultz .................... 356/375 |
| 5,921,992 A | | 7/1999 | Costales et al. ............. 606/130 |
| 6,152,933 A | * | 11/2000 | Werp et al. ............ 604/165.01 |
| 6,321,104 B1 | * | 11/2001 | Gielen et al. ................ 600/378 |

FOREIGN PATENT DOCUMENTS

| | | |
|---|---|---|
| DE | 198 32 296 A1 | 7/1998 |
| EP | 0 207 452 | 1/1987 |
| EP | 0 319 844 A1 | 12/1988 |
| EP | 0 651 968 A1 | 8/1990 |
| EP | 0 622 057 A2 | 4/1994 |
| EP | 0 919 202 A2 | 6/1999 |
| EP | 0 919 203 A2 | 6/1999 |
| GB | 2 094 590 A | 9/1982 |
| WO | WO 91/04711 | 4/1991 |
| WO | WO 91/07726 | 5/1991 |
| WO | WO 92/06645 | 4/1992 |
| WO | WO 94/23647 | 10/1994 |
| WO | WO 94/24933 | 11/1994 |
| WO | WO 96/11624 | 4/1996 |
| WO | WO 96/32059 | 10/1996 |
| WO | WO 97/49453 | 12/1997 |
| WO | WO 98/08554 | 3/1998 |
| WO | WO 98/38908 | 9/1998 |
| WO | WO 99/15097 | 4/1999 |

OTHER PUBLICATIONS

Reinhardt, et al., Sonic Stereometry in Microsurgical Procedures for Deep–Seated Brain Tumors and Vascular Malformations, Neurosurgery, Jan. 1993, 51–57, vol. 32, No. 1.

Reinhardt, Neuronavigation: A Ten–Year Review, Neurosurgery,__, 329–340,__.

Bucholz, et al., Intraoperative localization using a three dimensional optical digitizer, Proceedings of Clinical Applications of Modern Imaging Technology, 1993, 312–322, vol. 1894.

PIXSYS, 3–D Digitizing Accessories, magazine ad.

Adams, et al., Aide au Reperage Tridimensionel Pour la Chirurgie de la Base du Crane, Innov. Tech. Biol. Med., 1992, 409–424, vol. 13, No. 4. (Adams, et al., Orientation Aid for Head and Neck Surgeons, Innov. Tech. Biol. Med., 1992, 409–424, vol. 13, No. 4.).

Reinhardt, et al., Mikrochirurgische Entfernung tiefliegender Gefäßmißbildungen mit Hilfe der Sonar–Stereometrie, Ultraschall in Med,. 1991, 80–84, vol. 12.

Pelizzari, et al., Interactive 3D Patient–Image Registration, Information Processing in Medical Imaging, 1991, 132–141, Springer–Verlag Berlin Heidelberg, Germany.

Rosenbaum, et al. Computerized Tomography Guided Stereotaxis: A New Approach, Applied Neurophysiology, 1980, 172–173, vol. 43, No. 3–5.

Boëthius, et al., Stereotaxic computerized tomography with a GE 8800 scanner, Journal of Neurosurgery, 1980, 794–800, vol. 52, No. 6.

Yeates, Simplified and accurate CT–guided needle biopsy of central nervous system lesions, Journal of Neurosurgery, 1982, 390–393, vol. 57, No. 3.

Heilbrun, Computed Tomography–Guided Stereotactic Systems, Clinical Neurosurgery, __, 564–581.

Heilbrun, et al., Preliminary experience with Brown–Roberts–Wells (BRW) computerized tomography stereotaxic guidance system, Journal of Neurosurgery, 1983, 217–222, vol. 59.

Horner, et al., A Comparison of CT–Stereotaxic Brain Biopsy Techniques, Investigative Radiology, 1984, 367–373, vol. 19.

Reinhardt, A Computer Assisted Device for Intraoperative CT–Correlated Localization of Brain Tumors, European Surgical Research, 1988, 52–58, S. Karger medical and Scientific Publishers.

* cited by examiner

ANCHORING SYSTEM FOR A BRAIN LEAD

This application Claims the benefit of Provisional Application No. 60/099,119 filed Sep. 3, 1998.

FIELD OF THE INVENTION

The present invention relates to an anchoring system for use in neurostimulation techniques. More specifically, the present invention relates to a system for anchoring a brain stimulation lead within a cranial burr hole.

BACKGROUND OF THE INVENTION

The surgical implantation in the human brain of electrode leads to deliver electrical impulses and catheters to deliver drugs in order to provide various types of therapy is known. Electrical stimulation of the brain, for example, can be considered for use to treat chronic pain or movement disorders. Typically, such stimulation is accomplished by the insertion of a multi-electrode lead into the brain, with the electrodes positioned at the location within the brain indicated by the particular condition requiring treatment. Usually, the electrodes are located on the distal end of the lead and a connector is located on the proximal end of the lead, where the lead is connected to a pulse generator, which may be internally or externally powered.

In order to insert the lead into the patient's brain, a surgeon first drills a hole in the patient's cranium using a surgical burr. Typically, the hole is 12 to 14 mm in diameter. The surgeon installs a burr hole ring in the burr hole, inserts the lead into the ring and advances the lead through the burr hole ring into the brain. As the surgeon advances the electrode, a test stimulation pulse is delivered to the brain through the electrode and the patient's response is monitored. When the surgeon observes an appropriate response, the lead is appropriately placed. Placement of the electrode within the brain can be critical, as small changes in position can have an effect on the efficacy of the therapy. Therefore, some type of method for anchoring the lead in place, once the surgeon has determined the optimal location for the electrodes, is required.

Prior methods for anchoring the lead include the application of bio-compatible epoxy or the use of a mechanical anchoring device that is part of or connected to a burr hole ring. For example, U.S. Pat. No. 4,328,813 to Ray ("Ray") and U.S. Pat. No. 5,464,446 to Dressen et al. ("Dressen") and PCT patent application number WO 98/08554 by Knuth et al. ("Knuth"), all of which are incorporated into this document by this reference, describe anchoring systems that involve mechanical anchoring of the lead to a burr hole ring. An article by Jean Siegfried, M. D., Pierre Comte, Ph.D., and Remy Meier appearing in the August, 1983 issue of the Journal of Neurosurgery entitled "Intracerebral electrode implantation system" ("Siegfried") also describes an anchoring system that involves mechanical anchoring of the lead to a burr hole ring.

Ray describes an anchoring system including an externally threaded burr hole ring that defines a socket into which an anchoring plug is inserted once the lead is correctly positioned within the brain. The anchoring plug is described as being made of sufficiently resilient material that it can be inserted into the socket and deform to accommodate the thickness of the lead. The friction between the socket, the lead and the plug is said to prevent the lead from moving after the plug is inserted into the socket. The anchoring system described in Ray, however, has disadvantages. Because the lead is secured off center, it is difficult to support during installation by stereotactic surgical instruments, which can be used to guide the lead during implantation. Additionally, the lead is subject to movement after the surgeon determines that the lead is correctly positioned but before the surgeon installs the plug, because the lead is unsupported until the plug is actually installed. Finally, the action of installing the plug into the socket can cause movement of the lead.

Dressen describes an anchoring system including a socket with an axial aperture, a plug with a concentric axial aperture and an external circumferential groove, and a cap with means for anchoring the lead in a bent position. The Dressen system has at least the disadvantage of not allowing the lead to be securely anchored by bending it to lay it flat on the surface of the patient's skull. Dressen's system also requires anchoring by tightening a suture within the external circumferential groove in the plug. This suture may be inconsistently tightened and may loosen over time.

Knuth and Siegfried describe essentially similar anchoring systems, both of which include, among other elements: (1) a baseplate with a centrally located hole that is adapted to be connected to a burr hole; (2) a compression seal, also with a centrally located hole (e.g., a silicone rubber ring), that is located with its hole aligned with the hole through the baseplate; and (3) a compression screw with a centrally located hole that is used to compress the seal longitudinally so that the seal expands radially inward to engage and therefore anchor the lead. At least one disadvantage associated with the systems described in Knuth and Siegfried is that the twisting of the compression screw may twist the compression seal and thus dislocate the end of the lead before the lead is sufficiently anchored.

Thus, a need continues to exist for an anchoring system for a brain stimulation lead in which the lead is always secure and anchored without applying torsion or axial forces to the lead or otherwise moving the distal end of the lead after it is appropriately positioned.

SUMMARY OF THE INVENTION

The design and implementation of a brain lead anchoring system is generally described. The anchor assembly includes an anchoring mechanism within an anchor housing, which has threads on its outer surface so that the housing can be screwed into a burr hole made in the patient's cranium. The anchoring mechanism preferably includes three locking tabs, each of which moves radially in a channel in the anchor housing relative to the generally centrally located lead path. The locking tabs are spring-loaded in a closed or anchoring position.

The introducer instrument is a generally conical body with a conical aperture that extends axially through the instrument through which the lead is introduced into the anchor assembly and thus the patient's brain. The introducer instrument also has a distal end having retraction protrusions that fit into complementary slots through the anchor housing. The opening in the distal end of the introducer is large enough that the lead moves easily through the opening. As the introducer instrument is mated to the anchor assembly, the retraction protrusions slide through the slots in the anchor housing and into apertures in the locking tabs, which pushes the locking tabs radially away from the lead path into an open or installation position. When the introducer and anchor assembly are so mated, the conical aperture in the introducer instrument and the centrally located aperture in the anchor assembly define the path on which the lead is introduced into the patient's brain. The surgeon advances the lead along this lead path using a standard stereotactic frame or a skull mounted guiding device. The lead is advanced into the patient's brain until the distal end of the lead is correctly positioned. While the lead is still secured in this position within the guiding device, the surgeon activates a mechanism on the introducer instrument or axially withdraws the introducer instrument, causing the retraction protrusions to be withdrawn from the apertures in the locking tabs, which in turn causes the spring-loaded locking tabs to return to the anchoring position, thus "pinching" the lead and anchoring it into position. Thus, the lead is anchored while being supported and without applying torsion or axial forces to the lead.

After the lead is anchored by the locking tabs within the anchor assembly, the surgeon removes the introducer instrument, which exposes the top of the anchor assembly. The surgeon then bends the lead so that it lies in one of the radially extending channels in the top surface of the anchor housing. To complete the installation of the lead, the surgeon inserts the locking cap, which preferably has three locking protrusions extending from its distal surface, into the same slots through which the retraction protrusions of the introducer instrument were inserted. Unlike the retraction protrusions, the locking protrusions hold the locking tabs in the locking position to ensure that the lead remains anchored even if the biasing member that spring-loads the locking tabs closed loses its resilience. The installed locking cap also covers the aperture in the top of the anchor housing.

Additional objectives and advantages of the invention will be set forth in part in the description which follows, and in part will be obvious from the description, or may be learned by practice of the invention. The objectives and advantages of the invention will be realized and attained by means of the elements and combinations particularly pointed out in the appended claims.

The foregoing general description and the following detailed description are exemplary and explanatory only and are not restrictive of the invention, as claimed. The accompanying drawings, which are incorporated in and constitute a part of this specification, illustrate one embodiment of the invention and together with the description, serve to explain the principles of the invention.

BRIEF DESCRIPTION OF THE DRAWINGS

FIG. 5A is an exploded cross-sectional view of the embodiment of the introducer instrument of FIG. 4A taken along line 5a—5a;

DESCRIPTION OF THE PREFERRED EMBODIMENT

Reference will now be made in detail to an embodiment of the invention, which is illustrated in the accompanying drawings. Wherever possible, the same reference numbers will be used throughout the drawings to refer to the same or like parts.

Figure 1:
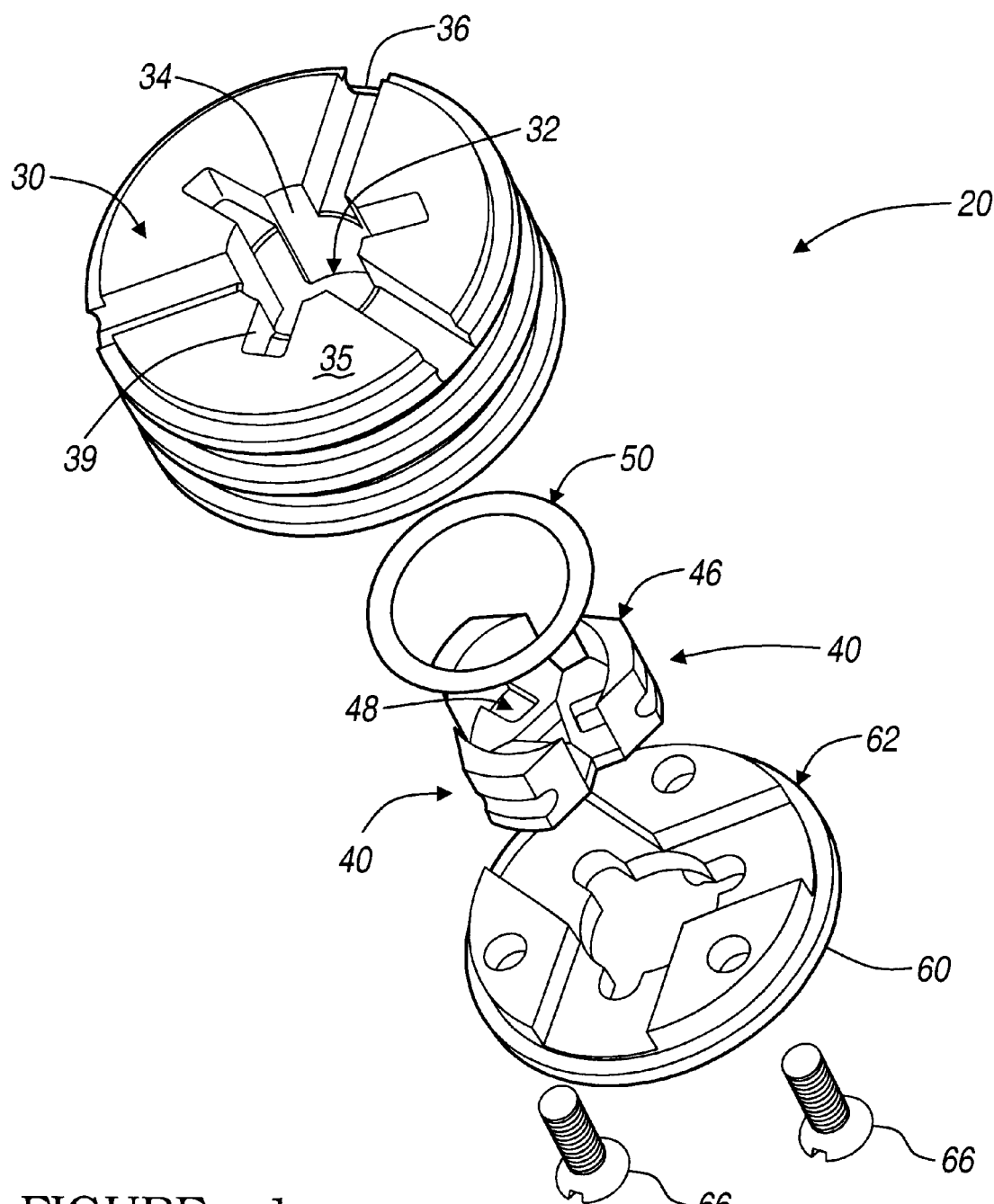
FIG. 1 is an exploded schematic perspective view of an anchor assembly of a brain lead anchoring system consistent with the present invention.

FIG. 1 is an exploded schematic perspective view generally from the proximal direction of the anchor assembly portion of the embodiment of a brain lead anchoring system constructed according to the present invention. A locking cap 70 (see FIG. 10), as discussed below, is used in connection with the anchor assembly 20. The anchor assembly includes an anchor housing 30, locking tabs 40 and anchor base 60, which all may be made of implant-grade titanium or stainless steel.

Figure 13:
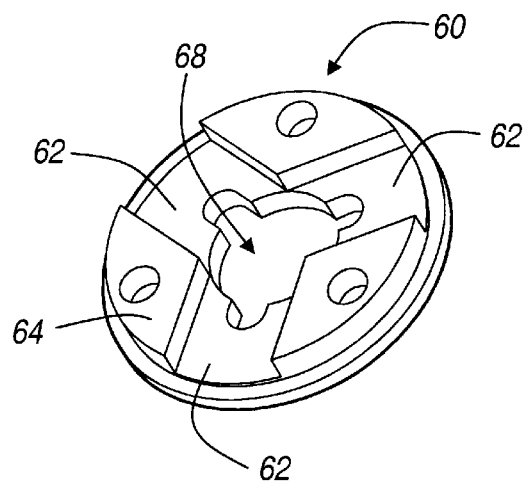
FIG. 13 is a schematic perspective view of the embodiment of the anchor base shown in FIG. 1.

Anchor housing 30 (which is further illustrated in FIGS. 6–9) is a generally cylindrical structure that has a cavity 33 defined therein. The anchor housing 30 has a large opening at one end and a smaller aperture 32 at the other end. Preferably, three locking tabs 40 are distributed circumferentially within cavity 33 and are biased radially inward toward an anchoring position by biasing member 50. Three locking tabs 40 are preferable because as locking tabs 40 move from the installation to the anchoring position, they automatically center lead 5 or a drug delivery catheter within aperture 32. After locking tabs 40 are positioned within anchor housing 30, anchor base 60 (FIG. 13) is connected, for example, via screws 66, to anchor housing 30 in order to enclose the open end of anchor housing 30. As perhaps best illustrated in FIG. 13, anchor base 60 includes three channels 62 evenly distributed on the inner surface 64 of anchor base 60 at approximately 120° angles. Anchor housing 30 includes three complementary channels 38 (see FIG. 8). Together, channels 62 in anchor base 60 and channels 38 in anchor housing 30 define three channels in anchor assembly 20 within which locking tabs 40 are free to move radially toward and away from the lead path, but not circumferentially, relative to longitudinal axis 37 (FIG. 7) of anchor housing 30.

Figure 12:
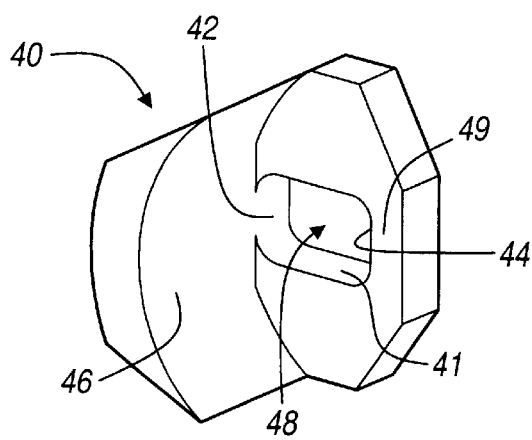
FIG. 12 is an enlarged, schematic perspective view of the embodiment of the locking tabs shown in FIG. 1.

Each of locking tabs 40 includes a tab stop 46 (FIG. 12) that interferes with a respective pair of anchor housing stops 34 (FIG. 7) to limit the radial movement toward longitudinal axis 37 of each locking tab 40 caused by biasing member 50. Biasing member 50 may be an elastomeric ring (e.g., made of bio-compatible natural or synthetic rubber), a radial spring made of an implant-grade titanium alloy or MPN35, or other suitable biasing structure known to those skilled in the art.

Figure 2A:
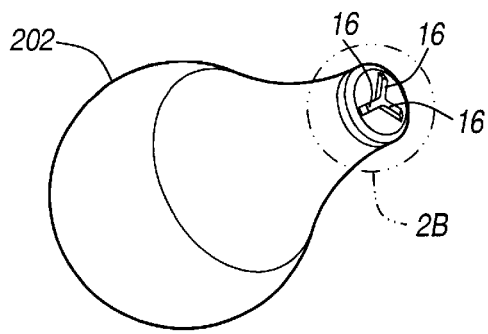
FIG. 2A is a perspective view of an anchor screwdriver for use with an anchor assembly of FIG. 1.
Figure 2B:
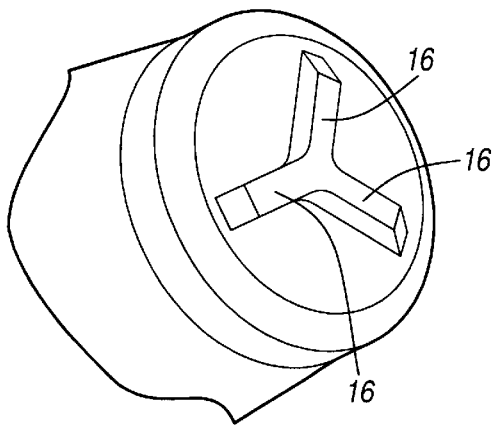
FIG. 2B is an enlarged view of the encircled portion of the anchor screwdriver of FIG. 2A.
Figure 2C:
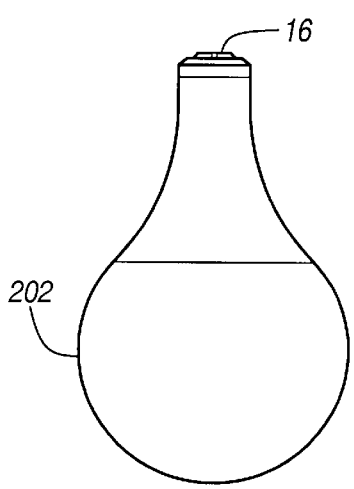
FIG. 2C is a side view of the anchor screwdriver of FIG. 2A.

The assembled anchor assembly 20 is anchored or screwed into a burr hole in a patient's skull using an anchor screwdriver. Referring to FIG. 2A, a bulb-shaped anchor screwdriver 202 is shown. The large or bulb end of the anchor screwdriver 202 is preferably sized to fit comfortably in a person's hand. The head or narrow end of the anchor screwdriver 202 has three installation tabs 16 on the head end of the anchor screwdriver 202. FIG. 2C shows a side view of the instrument screwdriver 202.

The installation tabs 16 fit into detents 36 in anchor housing 30 to enable the anchor screwdriver to turn the anchor assembly 20 when the anchor assembly 20 is positioned in a burr hole of a patient's skull. When the anchor screwdriver 202 is fully engaged with the anchor assembly 20, installation tabs 16 mate with detents 36 in the proximal end surface 35 of anchor housing 30. The installation tabs 16 enable the surgeon to use the anchor screwdriver 202 to turn anchor assembly 20 to implant or withdraw the anchor assembly 20 that is in the cranial burr hole in the patient's skull. (See FIG. 7 for a cross-sectional profile of threads 31.) Installation tabs 16 bear the twisting load applied when the surgeon uses the anchor screwdriver 202 to install or remove the anchor assembly 20.

Figure 3C:
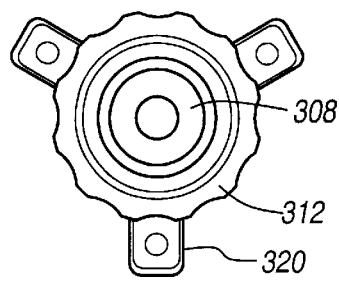
FIG. 3C is a top view of the introducer instrument of FIG. 3A.
Figure 3A:
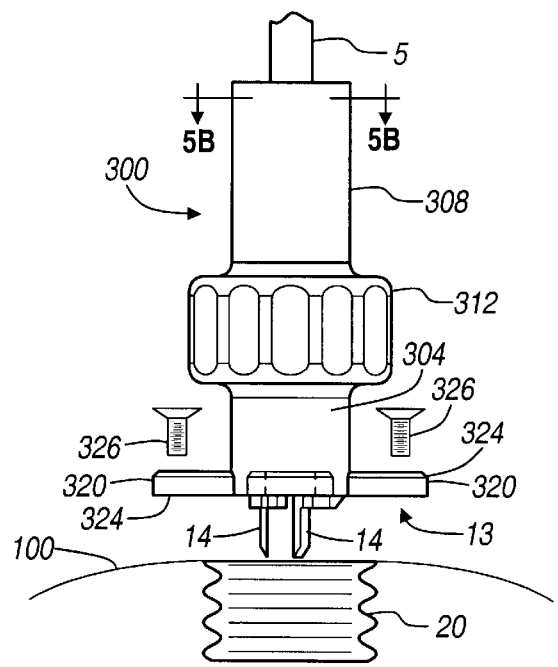
FIG. 3A is a side view of an embodiment of an introducer instrument consistent with the present invention.

Referring to FIG. 3A, after the anchor assembly 20 has been inserted or installed into a patient's cranium 100, an introducer instrument 300 is used to guide the lead 5 into and through anchor assembly 20 into the patient's skull. The introducer instrument 300 has three retraction protrusions 14 on the distal end 13 of the introducer instrument 300 to push out locking tabs 40 and retract the locking tabs 40 into the installation position. The introducer instrument 300 may be made of surgical stainless steel or aluminum.

Each of the distal ends of retraction protrusions 14 includes a retraction surface 15. As retraction protrusions 14 are advanced into slots 39 (FIGS. 5B and 8), each of retraction surfaces 15 comes into contact with a corresponding retraction surface 42 of the corresponding locking tab 40 and causes locking tabs 40 to be pushed radially outward from the anchoring position to the installation position. FIG. 9 depicts, for illustrative purposes only, two locking tabs 40b in the anchoring position and locking tab 40a in the installation position within anchor housing 30. Preferably, in operation, all locking tabs 40 move substantially simultaneously. The retraction protrusions 14 extends from a retractable introducer 402 (FIGS. 4A and 4B) of the introducer instrument 300 and are operative to slide axially relative to the introducer body. A distal end portion of the retraction protrusion extends from the distal end of introducer instrument 300.

Figure 4A:
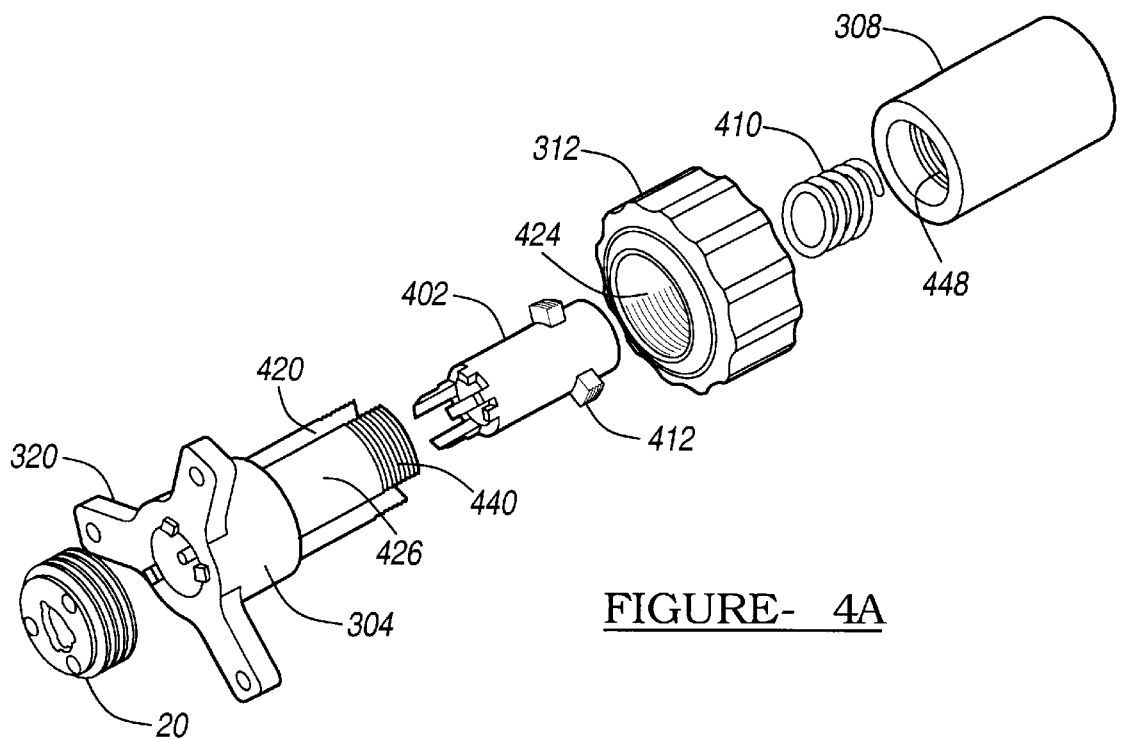
FIGS. 4A and 4B are exploded views of the introducer instrument of FIG. 3A from different perspectives.

The introducer instrument 300 includes an introducer guide channel 304, an introducer retaining sleeve 308, an introducer retraction knob 312, a retractable introducer 402 (FIG. 4A) and a spring 410 (FIG. 4A). The introducer guide channel 304 includes wing members 320 for use in securing the introducer instrument 300 to the skull 100. The wings 320 have screw holes 324 defined therein for receiving screws 326 that secure the instrument introducer 300 to the patient's skull. The screws 326 extend through the wings 320 into the patient's skull 100.

The introducer instrument 300 allows the surgeon to withdraw the retraction protrusions 14 while introducer instrument 300 and anchor assembly 20 are mated, which secures lead 5 within anchor assembly 20, without physically separating the distal end 13 of introducer instrument 300 from the top surface 35 of anchor housing 30. Thus, locking tabs 40 move from the installation position to the anchoring position without any other part of the system coming in contact with lead 5 and dislodging it.

As the introducer instrument 300 is mated to the anchor assembly 20, the retraction protrusions 14 slide through slots in the anchor housing and into apertures in the locking tabs 40, which pushes the locking tabs 40 radially away from the path of the lead 5 or a catheter into an open or installation position. When the introducer instrument 300 and anchor assembly 20 are mated, a conical aperture 530 (FIG. 5A) in the introducer retaining sleeve 308, a cylindrical channel 540 (FIG. 5A) and centrally located aperture in the anchor assembly define the path in which the lead 5 is introduced into the patient's brain. The surgeon advances the lead along this path using a standard stereotactic frame or a skull mounted guiding device. The lead 5 is advanced into the patient's brain until the distal end of the lead is correctly positioned. While the lead 5 is still secured in this position within the introducer instrument, the surgeon activates a mechanism on the introducer instrument 300 that causes the retraction protrusions 14 to be withdrawn from the apertures in the locking tabs. The withdrawal of the retraction protrusions 14, in turn, causes the spring-loaded locking tabs to return to the anchoring position, thus "pinching" the lead 5 and anchoring it into position. Thus, the lead is anchored while being supported by the introducer instrument 300.

Figure 3B:
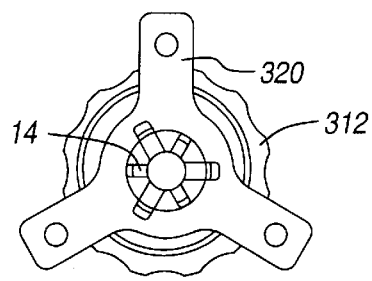
FIG. 3B is a bottom view of the introducer instrument of FIG. 3A.

The mechanism used to withdraw the retraction protrusions 14 is the introducer retraction knob 312. The introducer retraction knob 312 is preferably initially set to a position that causes the retraction protrusions 14 to be extended to the maximum distance away from the bottom of the introducer guide channel 304. The retraction knob 312 may be turned to cause the retraction protrusions 14 of the retractable introducer 402 (FIGS. 4A and 4B) to be withdrawn from the anchor assembly 20 as discussed above. FIG. 3B shows a bottom view of the introducer instrument 300 and FIG. 3C shows a top view of the introducer instrument 300.

Figure 4B:
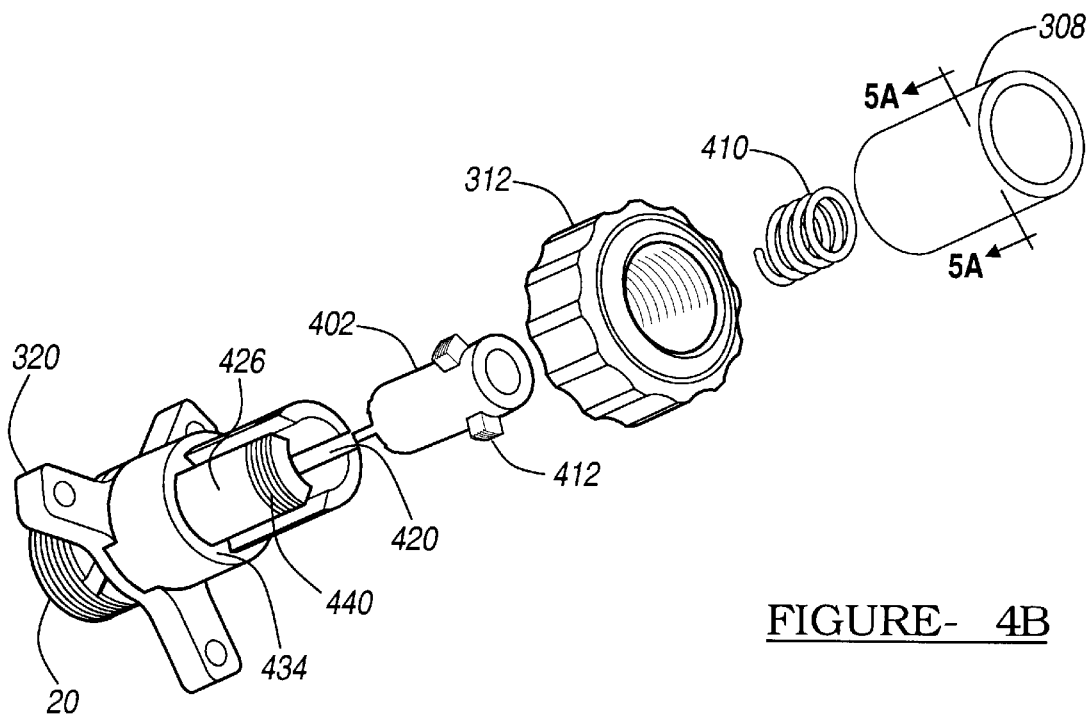

Referring to FIGS. 4A and 4B, exploded prospective views of the introducer instrument 300 are illustrated. As discussed above, the introducer instrument 300 includes the introducer retaining sleeve 308, spring 410 for preventing backlash during movement of the retractable introducer 402, an introducer retraction knob 312, and an introducer guide channel 304. The introducer retaining sleeve 308 has a conical aperture 530 (FIG. 5A) that directs the lead 5 into the body of the introducer instrument 300. The retractable introducer 402 has threaded protrusions 412 extending from the conical surface of the retractable introducer 402 at a proximal end of the retractable introducer 402. Each set of the threaded members are preferably evenly distributed at 120° intervals on the retractable introducer 402. At the distal end of the retractable introducer 402, the three retraction protrusions 14 are preferably evenly distributed at 120° intervals at the distal end of the retractable introducer 402 as illustrated. The threaded protrusions 412 of the retractable introducer 402 extend into corresponding locking channels 420 of the introducer guide channel 304.

The three locking channels 420 extend lengthwise along and through the arc-shaped sidewalls 426 of the introducer guide channel and are located at 120° intervals such that the threaded members 412 of the retractable introducer 402 slide into the locking channels 420 in a mating position. The introducer retraction knob 312 has threads 424 which mate with the threaded protrusions 412 of the retractable introducer 402. The introducer retraction knob 312 rests upon a shelf 434 of the introducer guide channel 304. By rotating the introducer retraction knob 312, the retractable introducer 402 is moved up or down corresponding to the direction of rotation of the introducer retraction knob 312. The introducer retaining sleeve 308, when assembled with the other components of the introducer instrument 300, attaches to threaded portions 440 of the arc-shaped sidewalls 426 that define the threaded guide channels. The introducer retaining sleeve 308 has threads 448 that screw onto the threaded protrusions 440 of the arc-shaped sidewalls 426 of the introducer guide channel.

Figure 5A:
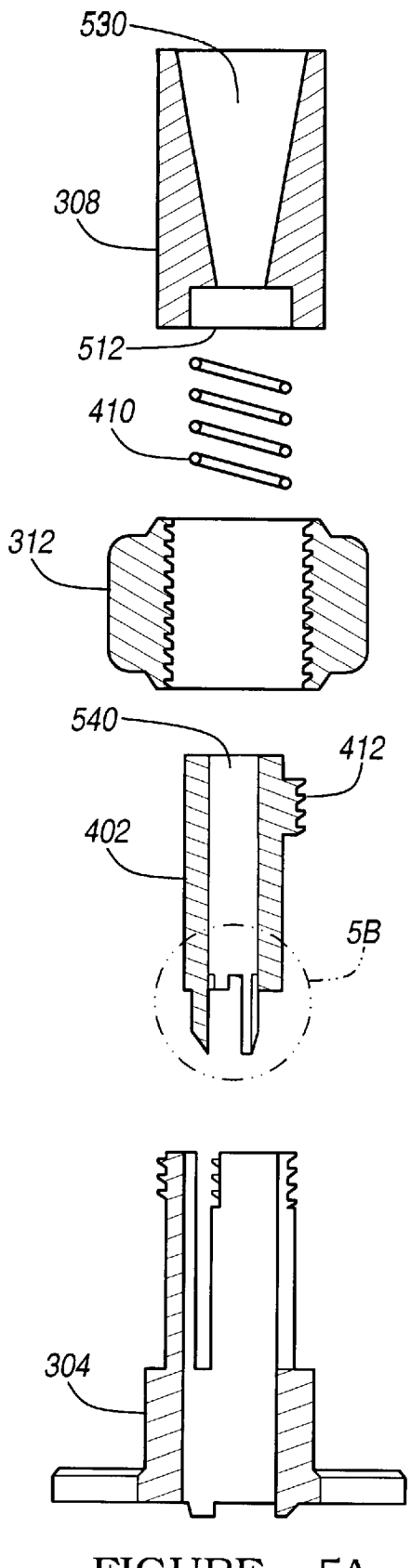
Figure 5B:
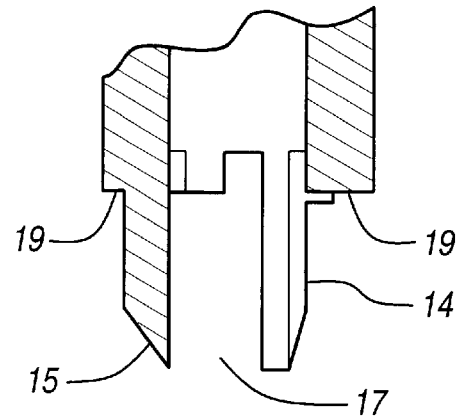
FIG. 5B is an enlarged view of the encircled portion of the embodiment of an introducer instrument shown in FIG. 5A.
Figure 5C:
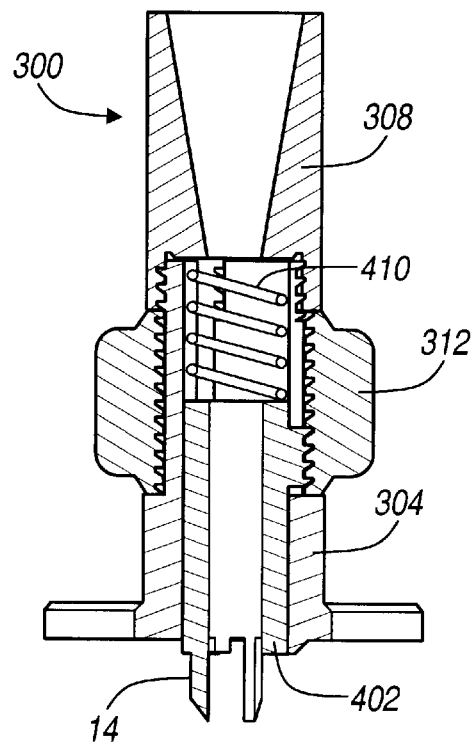
FIG. 5C is a cross-sectional view of the embodiment of an introducer instrument shown in FIG. 1 taken along line 5b—5b of FIG. 3A.

Referring to FIGS. 5A, 5B, and 5C, cross-sectional views of the introducer instrument are illustrated. FIG. 5A illustrates a cross-sectional view of the introducer element taken along line 5a—5a of FIG. 4B. The spring element 410 fits into the threaded channel 512 (FIG. 5A) of the instrument retaining sleeve 308 when the introducer instrument is assembled. FIG. 5B is an enlarged view of the encircled portion of introducer instrument 300. Retraction surfaces 15 are canted relative to the longitudinal axis 17 of the retractable introducer 402 in order to act as ramps on which retraction surfaces 42 of locking tabs 40 ride as retraction protrusions 14 are inserted into actuation apertures 48 (FIG. 12) of locking tabs 40. Once retraction protrusions 14 are fully advanced into actuation apertures 48, shoulders 19 at the base of retraction protrusions 14 come into contact with lands 49 (FIG. 12) of locking tabs 40 in order to prevent further advancement of retraction protrusions 14 through actuation apertures 48. FIG. 5C is a cross-sectional view of the assembled introducer instrument 300 taken along line 5b—5b of FIG. 3A.

Figure 6:
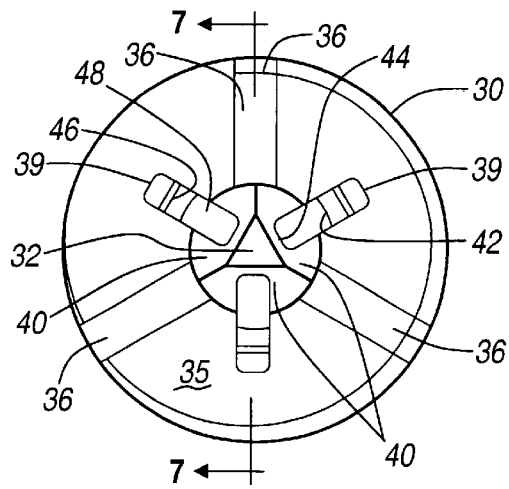
FIG. 6 is a top view of the embodiment of the anchor housing shown in FIG. 1 in which all locking tabs are shown in the anchoring position.
Figure 7:
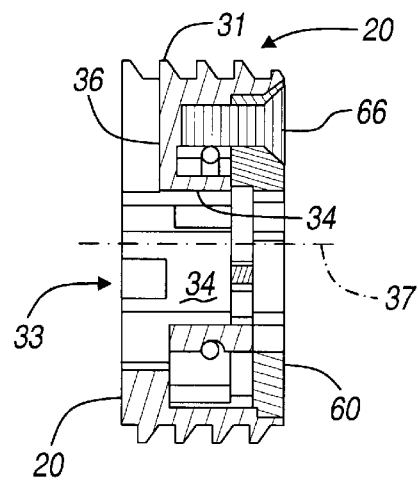
FIG. 7 is a cross-sectional view of the embodiment of the anchor housing and anchor base shown in FIG. 1, but assembled together taken along line 7—7 of FIG. 6.

FIG. 6 is a top view of anchor housing 30 in which all locking tabs 40 are shown in the anchoring position. The shape of lead aperture 32 is illustrated, along with the arrangement of slots 39 in lead aperture 32 and detents 36 in top surface 35 of anchor housing 30. Also illustrated, to a degree, is the arrangement within cavity 32 of locking tabs 40, a portion of which are visible through lead aperture 32.

Figure 8:
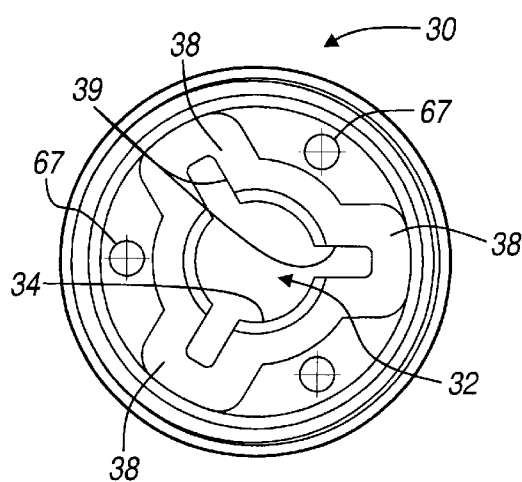
FIG. 8 is a bottom view of the embodiment of the anchor housing shown in FIG. 1 without locking tabs installed in the anchor housing.
Figure 9:
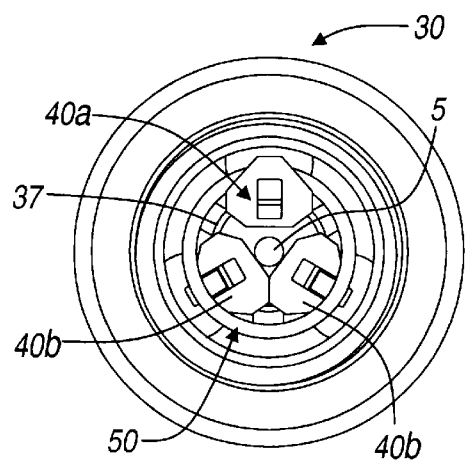
FIG. 9 is a bottom view of the embodiment of the anchor housing shown in FIG. 1 with locking tabs installed and two locking tabs in the anchoring position and one locking tab in the installation position.

FIG. 8 is a bottom view of anchor housing 30 with anchor base 60 removed and without locking tabs 40 installed in anchor housing 30. This view illustrates the distribution of slots 39 around the circumference of lead aperture 32 and the distribution of channels 38, and screw holes 67, all of which are distributed at approximately 120° intervals around anchor housing 30. Also clearly illustrated is the distribution of three anchor housing stops 34, which limit radial movement inward of locking tabs 40 within channels 38.

Figure 10:
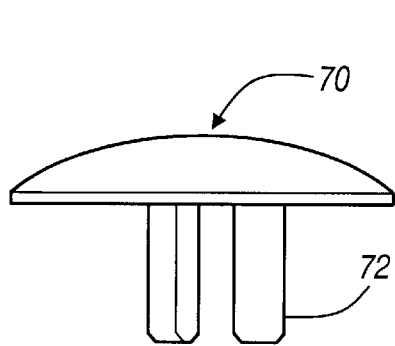
FIG. 10 is a side view of an embodiment of a locking cap that is compatible with the anchoring assembly shown in FIG. 1.
Figure 11:
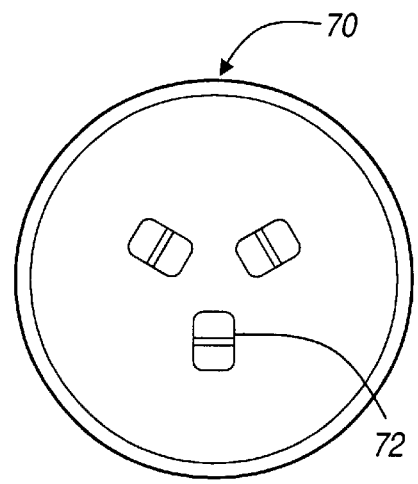
FIG. 11 is a bottom view of the locking cap shown in FIG. 10.

FIG. 10 is a side view of locking cap 70 for use in covering aperture 32 in anchor housing 30 and positively securing locking tabs 40 in the anchoring position in which three anchoring protrusions 72 are use. It should be recognized that two or more anchoring protrusions could be used. FIG. 11 is a bottom view of locking cap 70 in which the location of all three anchoring protrusions 72 is illustrated. After the surgeon positions lead 5 at the correct location within the patient's brain and withdraws introducer instrument 10 from anchor assembly 20, which causes locking tabs 40 to anchor lead 5, the external portion of lead 5 is folded into one of detents 36 in anchor housing 30 so that lead 5 is bent at approximately a 90° angle and the external portion of lead 5 (or a separate extension of lead 5) can be run along the surface of the patient's skull toward an implantable pulse generator. Once lead 5 is positioned in one of detents 36, anchoring protrusions 72 of locking cap 70 are inserted into anchor assembly 20 through slots 39 in anchor housing 30 and into actuation apertures 48 of locking tabs 40. The geometric arrangement of anchoring protrusions 72 causes them to force, via contact with locking surfaces 44, locking tabs 40 into the anchoring position. Thus, a reduction in resilience of biasing member 50 will not result in a reduction of the anchoring force that locking tabs 40 apply to lead 5.

The method of using the anchoring system according to the present invention is as follows. Once the burr hole in the patient's cranium is ready for installation of the anchor assembly, the surgeon mates introducer instrument 300 with anchor assembly 20 so that retraction protrusions 14 open locking tabs 40 to the installation position and installation tabs 16 fit within detents 36. The surgeon then uses the screwdriver 202 to screw anchor assembly 20 into the burr hole in the patient's cranium. The surgeon securely mounts lead 5 into a suitable guiding device and uses the guiding device to advance lead 5 into the patient's brain through the installation aperture 11, and lead aperture 32. The lead 5 is advanced into the patient's brain until the distal end of the lead is correctly positioned. While the guiding device is still securely holding lead 5 in this position, the surgeon activates a mechanism, such as te knob 312, on introducer instrument 300 or withdraws introducer instrument 300 from anchor assembly 20, causing retraction protrusions 14 to withdraw from actuation apertures 48. Biasing member 50 then causes locking tabs 40 to return to the anchoring position (see e.g., locking tabs 40b in FIG. 9), thus "pinching" lead 5 and anchoring it into position. This ensures that lead 5 does not move away from a proper position during the post-placement anchoring procedure.

After lead 5 is anchored by locking tabs 40 within anchor assembly 20, the surgeon removes the guiding device and introducer instrument 10, which exposes the top surface 35 of anchor housing 30. The surgeon then bends lead 5 so that it lies in one of detents 36 in anchor housing 30. To complete the installation of lead 5, the surgeon installs locking cap 70 by inserting anchoring protrusions 72 into slots 39 and through actuation apertures 48 in locking tabs 40. Unlike retraction protrusions 14 of introducer instrument 10, locking protrusions 72 force locking tabs 40 into the anchoring position (see, e.g., locking tabs 40b in FIG. 9) to anchor lead 5 even if biasing member 50 loses resilience. The installed locking cap 70 also covers lead aperture 32 in anchor housing 30. After locking cap 70 is installed, lead 5 is ready to be connected to an appropriate pulse generator.

It will be apparent to those skilled in the art that various modifications and variations can be made in the anchoring system of the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A brain lead anchoring system, comprising:

a. an introducer instrument comprising:
      an introducer body defining a first lead aperture,
      a retraction protrusion located on the introducer body; and b. an anchor assembly, comprising:
   an anchor housing defining a second lead aperture that, along with the first lead aperture, defines a lead path through the brain lead anchoring system, and
   a movable locking tab located proximate the lead path and having a retraction surface that is adapted to cooperate with the retraction protrusion of the introducer instrument to retract the locking tab from an anchoring position to an instrument installation position.

2. The brain lead anchoring system of claim 1, further comprising a biasing member connected to the locking tab in a manner to bias the locking tab toward the anchoring position.

3. The brain lead anchoring system of claim 2, in which the biasing member is a spring.

4. The brain lead anchoring system of claim 2, in which the biasing member is an elastomeric ring.

5. The brain lead anchoring system of claim 2, in which the introducer instrument further comprises a means for manually disengaging the retraction protrusion from the locking tab so that the locking tab returns to the anchoring position.

6. The brain lead anchoring system of claim 1, further comprising:
   a. a locking surface on the locking tab and
   b. a locking cap having an anchoring protrusion that cooperates with the locking surface to position the locking tab in the anchoring position.

7. The brain lead anchoring system of claim 6, further comprising an anchor base connected to the anchor housing such that the anchor base and the anchor housing define a cavity within which the locking tabs are substantially enclosed.

8. The brain lead anchoring system of claim 7, in which the retraction surface of the locking tab is a portion of an actuation surface defining an actuation aperture in the locking tab.

9. The brain lead anchoring system of claim 8, in which:
   a. the anchor housing further comprises an anchor housing stop located within the cavity; and
   b. the locking tab further comprises a tab stop positioned to cooperate with the anchor housing stop in order to limit the movement of the locking tab in a radial direction relative to the lead path.

10. The brain lead anchoring system of claim 9, in which:
   a. the anchor housing further comprises a first radial channel within the cavity;
   b. the anchor base further comprises a second radial channel within the cavity and aligned with the first radial channel; and
   c. the first and second radial channels limit the movement of the locking tab in a circumferential direction relative to the lead path.

11. The brain lead anchoring system of claim 10, in which the anchor housing further comprises a detent defining a lead exit path that extends at least radially from the lead path.

12. The brain lead anchoring system of claim 11, further comprising an anchor screwdriver that has an installation tab that is positioned such that it mates with at least a portion of the detent in the anchor housing when the anchor screwdriver is engaged with the anchor housing to insert or withdraw the anchor housing from the cranium of a patient.

13. A brain lead anchoring system, comprising:
   a. an anchor assembly, comprising:
      an anchor housing defining a first lead aperture,
      at least one anchor within or connected to the anchor housing operative to anchor a lead, the at least one anchor movable between an installation position and an anchoring position, and
      a biasing member connected to the at least one anchor to bias the at least one anchor toward the anchoring position; and
   b. an introducer instrument comprising:
      an introducer body defining a second lead aperture that, along with the first lead aperture, defines a lead path through the brain lead anchoring system, and
      a retraction protrusion located on the introducer body operative to retract the at least one anchor from the anchoring position to the installation position.

14. The brain lead anchoring system of claim 13, further comprising a lock to positively lock the at least one anchor in the anchoring position independently of the biasing member.

15. The brain lead anchoring system of claim 13, further comprising an anchor base connected to the anchor housing such that the anchor base and the anchor housing define a cavity within which the at least one anchor is substantially enclosed.

16. The brain lead anchoring system of claim 15, in which the anchor assembly further comprises guide paths that limit the movement of the at least one anchor in a radial direction relative to the lead path.

17. The brain lead anchoring system of claim 16, in which the anchor assembly further comprises guide channels that limit the movement of the at least one anchor in a circumferential direction relative to the lead path.

18. The brain lead anchoring system of claim 17, in which the anchor housing further comprises a detent defining a lead exit path that extends at least radially, from the lead path.

19. The brain lead anchoring system of claim 18, in which the introducer instrument further comprises an installation tab that is positioned such that it mates with at least a portion of the detent in the anchor housing when the introducer instrument is engaged with the anchor housing.

20. The brain lead anchoring system of claim 13, in which the biasing member is a spring.

21. The brain lead anchoring system of claim 13, in which the biasing member is an elastomeric ring.

22. The brain lead anchoring system of claim 13, in which the introducer instrument further comprises a knob that is operative to disengage the retraction protrusions from the at least one anchor so that the at least one anchor returns to the anchoring position.

* * * * *

UNITED STATES PATENT AND TRADEMARK OFFICE
CERTIFICATE OF CORRECTION

PATENT NO.     : 6,482,182 B1                                          Page 1 of 1
DATED          : November 19, 2002
INVENTOR(S)    : Carroll et al.

It is certified that error appears in the above-identified patent and that said Letters Patent is hereby corrected as shown below:

<u>Title page, Item [54] and Column 1, line 1,</u>
Title, after "BRAIN" insert -- STIMULATION --.

<u>Column 7,</u>
Line 57, "use" should be -- used --.

<u>Column 8,</u>
Line 27, "te" should be -- the --.

Signed and Sealed this

Twenty-seventh Day of January, 2004

JON W. DUDAS
*Acting Director of the United States Patent and Trademark Office*